United States Patent [19]

Frantsits

[11] 3,997,558
[45] Dec. 14, 1976

[54] PROCESS OF PRODUCING 1-ACYL-2-METHYL-INDOLYL-3-ALKANOIC ACIDS

[76] Inventor: Werner J. Frantsits, Boltzmanngasse 9a-11, Vienna 9, Austria

[22] Filed: July 24, 1975

[21] Appl. No.: 598,835

[30] Foreign Application Priority Data

Dec. 18, 1974 Austria .................... 10094/74

[52] U.S. Cl. .................... 260/326.13 A
[51] Int. Cl.$^2$ ............ C07D 209/26; C07D 209/28
[58] Field of Search .................... 260/326.13 A

[56] References Cited

FOREIGN PATENTS OR APPLICATIONS 1,620,358      Germany
1,643,463      Germany

*Primary Examiner*—Lewis Gotts
*Assistant Examiner*—S. P. Williams
*Attorney, Agent, or Firm*—Martin A. Farber

[57] ABSTRACT

The process is directed to the production of 1-acyl-2-methyl-indolyl-3-alkanoic acids having the general formula

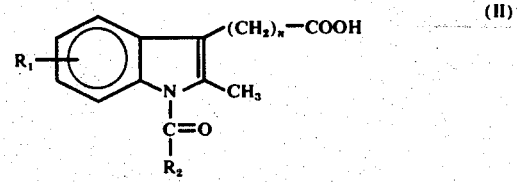

wherein $R_1$ represents hydrogen, halogen, an alkoxy group or an aryloxy group, $n$ is 1, 2 or 3, and $R_2$ represents an aromatic group. A lactone having the general formula

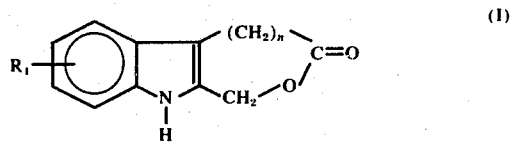

wherein $R_1$ and $n$ have the meanings stated above, is acylated by being reacted in a polar solvent in the presence of sodium hydride with an acid derivative having the general formula

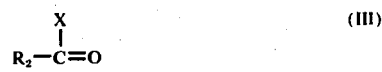

wherein $R_2$ has the meaning stated above and X represents a halogen, to form a compound having a lactone ring and having the general formula

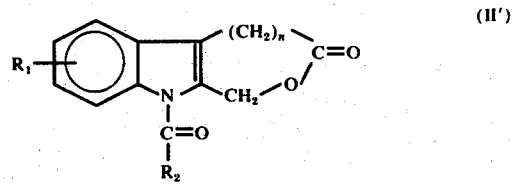

wherein $R_1$, $R_2$, and $n$ have the meanings stated above. The last-mentioned compound is hydrogenolyzed in the presence of a hydrogenation catalyst to open the lactone ring.

9 Claims, No Drawings

PROCESS OF PRODUCING 1-ACYL-2-METHYL-INDOLYL-3-ALKANOIC ACIDS

A large number of processes are known for the production of N-acylated indolylcarbocylic acid derivatives, which have valuable therapeutic properties.

In the process according to the invention, a lactone having the general formula

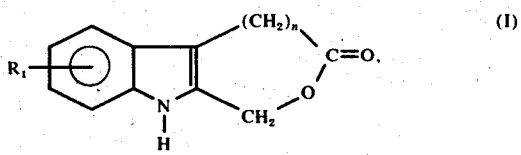

wherein $R_1$ represents hydrogen, halogen, an alkoxy, preferably methoxy group, or an aryloxy, preferably phenoxy group, and $n$ is 1, 2 or 3, is reacted in the presence of sodium hydride in a polar solvent (e.g., dimethylformamide) with an aromatic acid halide, preferably an acid chloride and which is substituted, if desired, by a halogen or a thiocyanate alkyl or aryl group. This results in a N-acylated lactone of the general formula.

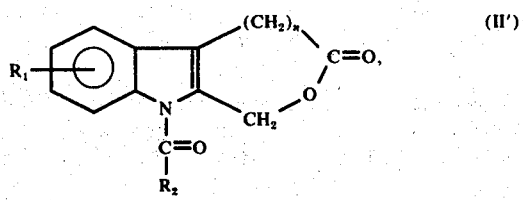

wherein $R_1$ and $n$ have the meanings stated above and $R_2$ represents an aromatic group, which is preferably a phenyl group and which is substituted, if desired, by a halogen, preferably chlorine or by a thiocyanate, alkyl or aryl group preferably a phenyl group. This N-acylated lactone is hydrogenolytically transformed into the corresponding 1-acylated indolyl-3-alkanoic acid.

Various methods are known for the production of the compound to be produced according to the invention. Conventionally the indolylacetic acid from which the desired compound is to be derived is produced in that the five-membered ring is first formed by a condensation step and with inclusion of the phenyl ring and the N-acyl group is subsequently introduced. The last-mentioned step has given rise to considerable difficulties unless the carboxylic acid group is protected because N-acylated compounds are likely to be decomposed under the action of strong acids and bases and the acetic acid group of indolylacetic acid imparts a strongly acid character to the indole derivative. The protective group which is introduced must be more easily separable than the N-acyl group. So far, only two groups have been proposed which are suitable for this purpose. These are the benzyl group and the tertiary butyl group. Whereas the benzyl group can be separated by a catalytic reduction, the yield of the desired compound is relatively low. The tertiary butyl group can be removed by pyrolysis but the resulting product is colored and can be purified only with considerable losses. For this reason it has already been proposed to subject a previously N-acylated phenylhydrazine to the Fischer synthesis of indole (e.g., Printed German Applications 1,620,358 and 1,643,463). That method has the disadvantage that it is difficult to acylate phenylhydrazine and that the rearrangement of phenylhydrazine which accompanies the cyclization is hindered by the substituent at the hydrazine residue so that secondary reactions take place and a highly contaminated product is obtained.

In the process proposed in the Austrian Patent specification 285,597 for the production of the compound which is to be produced according to the invention, a corresponding indole-2,2:3',4'-dihydrothiophene derivative is catalytically reduced. For this purpose, the dihydrothiophene derivatives are boiled in ethanol with hydrogen-saturated Raney nickel. This reaction requires high temperatures and the resulting raw product contains impurities which can be separated only with difficulty. An additional disadvantage of the process resides in that the Raney nickel cannot be recycled in the process owing to the secondary reaction with hydrogen sulfide, which is a strong catalyst poison.

In the process according to the invention the carboxylic group is protected in a lactone. This results in several advantages, which are of high technological significance because the ring can be opened by hydrogenolysis at room temperature and because the used catayst can be recycled in the process.

An additional advantage afforded by the process according to the invention over the known processes resides in that the hydrogenolysis does not result in a second product which would have to be removed or recovered by special additional processes.

Besides, the process results in high yields (about 95%) and requires only short reaction times and requires thermal energy only for the cooling which is required during the acylation.

The lactone may be produced in that, e.g., the corresponding oxolactone is reacted with the corresponding phenylhydrazine in the presence of acid. Higher-membered lactones may alternatively be produced by an oxidation of cyclic ketones with peroxo acids.

The invention will now be explained more fully with reference to a non-limiting example. In connection therewith, a method of producing a starting product for the process according to the invention will be explained.

EXAMPLE

Production of 1-(p-chlorobenzoyl)-2-methyl-5-methoxyindolyl-3-acetic acid a. Production of the lactone of 5-methoxy-2-hydroxymethyl-indolyl-3-acetic acid:

0.1 mole (24 grams) 4-methoxyphenylhydrazinesulfonic acid sodium having the formula

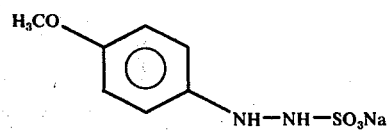

and 0.1 mole (11.1 g) 4-oxo-δ valerolactone having the formula

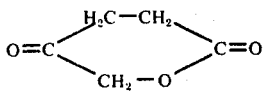

are refluxed in tetrahydrofurane with HCL for some hours. The tetrahydrofurane is then distilled off and ether is added. The resulting mixture is washed with aqueous sodium hydrogen carbonate solution and finally with water. The ether is distilled off and the residue is chromatographically purified (stationary phase: silicum dioxide; liquid phase: benzene).

The residue is the lactone of 5-methoxy-2-hydroxymethyl-indolyl-3-acetic acid and has the formula

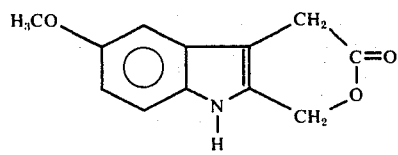

The starting substances have been repeatedly described in the literature.

b. Lactone of 1-(p-chlorobenzoyl)-5-methoxy-2-hydroxymethyl-indolyl-3-acetic acid:

0.01 mole (2.17 g) lactone of 5-methoxy-2-hydroxymethyl-indolyl-3-acetic acid are added at 0° C to a suspension of 0.01 mole (0.24 g) sodium hydride in 20 ml, N,N-dimethylformamide. The mixture is stirred for one hour. 0.01 mole (1.4 g) p-chlorobenzoyl chloride is then added gradually in drops within two hours. When this addition has been completed, the stirring of the mixture is continued for 1 hour at 0° C. The organic phase is then washed with water and with aqueous NaHCO₃ solution and is dried over magnesium sulfate, whereafter the solvent is removed by vacuum distillation. Yield: 2.5 g of a yellowish oil.

c. 1-(p-chlorobenzoyl)-2-methyl-5-methoxyindolyl-3-acetic acid:

1.05 g of the product of (b) are dissolved in 20 ml tetrahydrofurane. 150 mg palladium on barium sulfate are added to the solution. The resulting mixture is hydrogenated under normal pressure. The resulting mixture is filtered and the solvent is removed by vacuum distillation. The residue is received in ether. From the resulting mixture, the acid is extracted with aqueous sodium hydrogen carbonate solution and is then precipitated with dilute phosphoric acid. The precipitate is dried. Yield: 1 g 1-(p-chlorobenzoyl)-2-methyl-5-methoxy-indolyl-3-acetic acid (formular IV).

Melting point 151°–152° C.

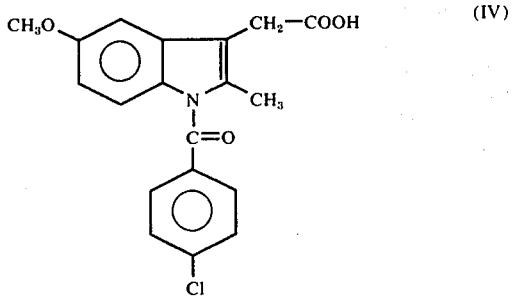

What is claimed is:

1. A process of producing 1-acyl-2-methyl-indolyl-3-alkanoic acids having the general formula

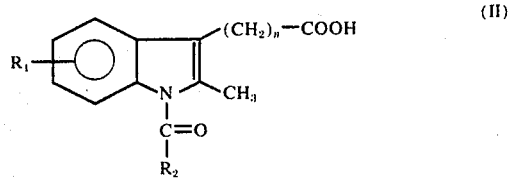

wherein $R_1$ represents hydrogen, halogen, an alkoxy group or an aryloxy group, $n$ is 1, 2 or 3, and $R_2$ represents an aromatic group, in which a lactone having the general formula

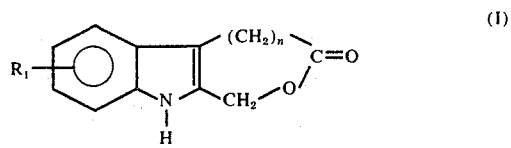

wherein $R_1$ and $n$ have the meanings stated above, is acylated by being reacted in a polar solvent in the presence of sodium hydride with an acid derivative having the general formula

wherein $R_2$ has the meaning stated above and X represents a halogen, to form a compound having a lactone ring and having the general formula

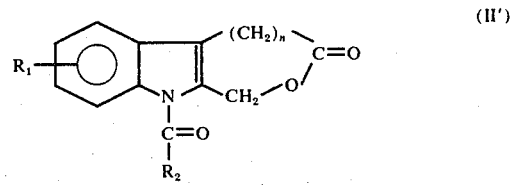

wherein $R_1$, $R_2$, and $n$ have the meanings stated above, and the last-mentioned compound is hydrogenolyzed in the presence of a hydrogenation catalyst to open the lactone ring.

2. A process as set forth in claim 1, in which $R_1$ represents a methoxy group.

3. A process as set forth in claim 1, in which $R_1$ represents a phenoxy group.

4. A process as set forth in claim 1, in which $R_2$ represents a phenyl group.

5. A process as set forth in claim 1, in which $R_2$ represents an aromatic group which is substituted by a halogen preferably chlorine or by a thiocyanate, alkyl or aryl group.

6. A process as set forth in claim 1, in which X represents chlorine.

7. A process as set forth in claim 1, in which said last-mentioned compound is hydrogenolyzed by being hydrogenated under normal pressure in the presence of a hydrogenation catalyst consisting of palladium deposited on barium sulfate.

8. A process as set forth in claim 1 for the production of 1-(p-chlorobenzoyl)-2-methyl-5-methoxy-indolyl-3-acetic acid, in which a lactone having the general formula (I), wherein $n$ is 1 and $R_1$ represents a methoxy group at carbon atom 5, reacted with an acid derivative having the general formula (III), wherein $R_2$ represents a p-chlorophenyl group and X represents a halogen, to form a compound having the general formula (II'), wherein $R_1$, $R_2$, and $n$ have the meanings defined in this claim, and the last-mentioned compound is hydrogenolyzed in the presence of a hydrogenation catalyst to open the lactone ring.

9. A process as set forth in claim 8, in which X represents chlorine.